(12) United States Patent
Suzuki et al.

(10) Patent No.: US 6,420,419 B1
(45) Date of Patent: *Jul. 16, 2002

(54) L-ASCORBIC ACID 2-PHOSPHATE ZINC SALT AND PROCESS FOR MANUFACTURING THE SAME

(75) Inventors: Masahiro Suzuki; Toshi Tsuzuki, both of Chiba; Shinobu Ito; Eiji Ogata, both of Tokyo, all of (JP)

(73) Assignee: Showa Denko Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/095,895

(22) Filed: Jun. 11, 1998

Related U.S. Application Data
(60) Provisional application No. 60/064,737, filed on Nov. 6, 1997.

(51) Int. Cl.[7] ............ A61K 31/341; C07D 307/33
(52) U.S. Cl. .............. 514/474; 549/477; 549/479; 549/497
(58) Field of Search ............... 549/477, 479, 549/497; 514/474

(56) References Cited

U.S. PATENT DOCUMENTS
3,671,549 A    6/1972  Hinkley
5,516,919 A  * 5/1996  Sano et al.

FOREIGN PATENT DOCUMENTS
FR    1489249    10/1967

\* cited by examiner

*Primary Examiner*—T. A. Solola
(74) *Attorney, Agent, or Firm*—Sughrue Mion, PLLC

(57) ABSTRACT

L-Ascorbic acid 2-phosphate zinc salt and a salt hydrate thereof having excellent solubility and exhibiting good stability even under weakly acidic conditions. Also disclosed is a process of manufacturing L-ascorbic acid 2-phosphate zinc salt by displacing a cation of a salt of an L-ascorbic acid 2-phosphate other than a zinc salt with a zinc cation. Further disclosed is a composition containing L-ascorbic acid 2-phosphate zinc salt or a salt hydrate thereof as an active ingredient.

18 Claims, No Drawings

L-ASCORBIC ACID 2-PHOSPHATE ZINC SALT AND PROCESS FOR MANUFACTURING THE SAME

CROSS REFERENCE TO RELATED APPLICATIONS

This application is an application filed under 35 U.S.C. §111(a) claiming benefit pursuant to 35 U.S.C. §119(e) (1) of the filing date of the Provisional Application 60/064,737 filed Nov. 6, 1997 pursuant to 35 U.S.C. §111(b).

FIELD OF THE INVENTION

The present invention relates to a novel L-ascorbic acid 2-phosphate salt, a process for manufacturing the salt and a method of use thereof. More specifically, the present invention relates to L-ascorbic acid 2-phosphate zinc salt or a salt hydrate of zinc L-ascorbic acid 2-phosphate (hereinafter, unless otherwise indicated, the salt including the salt hydrate thereof is referred to as an "L-ascorbic acid 2-phosphate zinc salt") which is a soluble L-ascorbic acid 2-phosphate salt having improved stability. L-ascorbic acid 2-phosphate zinc salt does not cause an extreme alkaline condition on dissolving in water and also exhibits antimicrobial activity. The present invention also relates to a method for manufacturing the salt and a method of use thereof. By using this salt, an L-ascorbic acid 2-phosphate-containing preparation (e.g., a cosmetic preparation, medical preparation, agricultural chemical preparation, animal drug preparation, foodstuff preparation and feedstuff preparation) having improved solubility, stability and antimicrobial properties (including antiseptic, deodorizing and antidandruff effects) and which is stable under weakly acidic conditions, can be obtained.

BACKGROUND OF THE INVENTION

L-Ascorbic acid (vitamin C) imparts many physiological effects. For example, vitamin C restrains lipid peroxide, accelerates the formation of collagen, retards the formation of melanin and enhances immune functions, and has hitherto been used to achieve these effects in the fields of medicine, agricultural chemicals, animal drugs, foodstuffs, feedstuffs and cosmetic preparations. Many preparations containing L-ascorbic acid are commercially available. However, L-ascorbic acid has poor aging stability, and the effect of vitamin C cannot be always obtained even if such a preparation is used.

In order to improve stability, derivatives obtained by converting the hydroxyl groups in the enediol moiety at the 2- or 3-position each into a glycosyl group (for example, JP-A-5-117290 (the term "JP-A" as used herein means an "unexamined published Japanese patent application")) or into a phosphoric acid ester (for example, JP-B-52-18191 (the term "JP-B" as used herein means an "examined Japanese patent publication") and JP-A-2-279690) have been proposed.

However, L-ascorbic acid 2-glycoside salts are converted into L-ascorbic acid in vivo (particularly in humans) at a low rate as compared with L-ascorbic acid 2-phosphates. Therefore, a prompt effect cannot be achieved and an adequately high vitamin C effect can hardly be obtained.

L-Ascorbic acid 2-phosphates provide a prompt effect, and an adequately high vitamin C effect can be easily obtained. However, conventionally known L-ascorbic acid 2-phosphates are a magnesium salt, a calcium salt and a sodium salt, and among these salts, L-ascorbic acid 2-phosphate magnesium salt having excellent stability does not have sufficiently high solubility in water and is difficult to form into an aqueous solution having a concentration of 30% or more. The calcium salt scarcely dissolves in water.

Sodium L-ascorbic acid 2-phosphate having satisfactorily improved solubility can be easily formed into an aqueous solution having a concentration of about 30%, but does not have a stability that is comparable with that of the magnesium salt. Furthermore, when dissolving any of these salts, the pH of the resulting solution is in an alkaline region of approximately from 8 to 10. When the pH is adjusted to a weakly acidic condition, the stability is disadvantageously lowered.

Although the above-described L-ascorbic acid derivatives have been proposed, an L-ascorbic acid 2-phosphate having excellent solubility and which is sufficiently stable even under weakly acidic conditions has not yet been obtained.

In obtaining a salt in general, neutralization of an acid or base is used in many cases. However, this method is not appropriate for manufacturing an L-ascorbic acid 2-phosphate salt on an industrial scale. This is because an L-ascorbic acid 2-phosphate solution is strongly acidic and unstable.

SUMMARY OF THE INVENTION

It is therefore an object of the present invention to provide an L-ascorbic acid 2-phosphate having excellent solubility and which exhibits sufficiently improved stability even under weakly acidic conditions.

Under these circumstances, the present inventors have conducted extensive investigations and as a result, have found that hitherto unknown L-ascorbic acid 2-phosphate zinc salt is a compound having highly improved solubility and stability even under weakly acidic conditions, and also provides an antimicrobial (antiseptic) effect.

The above object of the present invention has been achieved by providing L-ascorbic acid 2-phosphate zinc salt and a salt hydrate of zinc L-ascorbic acid 2-phosphate which, in addition to the above properties, has also been found to have an antimicrobial effect. The present invention further provides a process for manufacturing the L-ascorbic acid 2-phosphate zinc salt and salt hydrate thereof and a method of using the salt and salt hydrate thereof in cosmetic and medical preparations, agricultural chemical preparations, animal drug preparations, foodstuff preparations and feedstuff preparations so as to increase the action of vitamin C or to provide an antimicrobial, antiseptic, deodorizing or antidandruff effect.

DESCRIPTION OF THE PREFERRED EMBODIMENTS

Examples of the process for manufacturing the compound of the present invention include a manufacturing process starting from a soluble L-ascorbic acid 2-phosphate salt and using an ion exchange technique or the like, and a combination of this manufacturing process with other purification methods, as needed. However, the present invention is by no means limited thereto.

If L-ascorbic acid 2-phosphoric acid is represented by $ApH_3$, the zinc salt of the present invention is represented by $Ap_2Zn_3$ and has a structure as shown in formula (1) below:

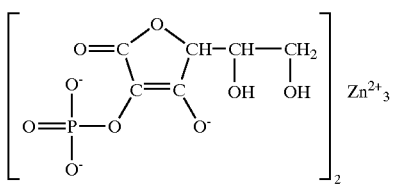
(1)

$Ap_2Zn_3$ is white powder and can be obtained as an anhydrite or salt hydrate. The salt hydrate is considered to be a hydrate $Ap_2Zn_3 \cdot nH_2O$ of $Ap_2Zn_3$.

In a preferred embodiment of the L-ascorbic acid 2-phosphate zinc salt or salt hydrate thereof of the present invention, 95 mol % or more of the entire cationic charge constitutes zinc ion and 95 mol % or more of the entire anionic charge constitutes L-ascorbic acid 2-phosphate ion. The Zn cation and Ap anion are present in sufficient amounts if each is contained in total in the above-described amounts. For example, when $Ap_2Zn_3$ is present in an amount of 95 mol % or more of the total L-ascorbic acid 2-phasphate salt content, $Ap_2Zn_2Mg$ or the like may be present in part. However, this is acceptable if the zinc ion content is 95 mol % or more of the total cation content.

The L-ascorbic acid 2-phosphate zinc salt of the present invention may be manufactured by a process using, for example, a soluble L-ascorbic acid 2-phosphate salt other than the zinc salt, such as $Ap_2Mg_3$, as a starting material and replacing the magnesium with zinc by chemical reaction or using an ion exchange technique (e.g., treating with an ion exchange resin). This process may also be combined with a purification method. Examples of the chemical reaction include:

$$Ap_2Mg_3 + 3ZnCl_2 \rightarrow Ap_2Zn_3 + 3MgCl_2$$

In a manufacturing process using an ion exchange technique, the soluble L-ascorbic acid 2-phosphate salt used as a starting material is not necessarily purified, but may be, for example, an L-ascorbic acid 2-phosphate-containing solution obtained by reacting L-ascorbic acid with phosphorus oxychloride. The ion exchange step may employ, for example, cation exchange column chromatography or anion exchange chromatography.

When using cation exchange column chromatography, an aqueous L-ascorbic acid 2-phosphate zinc salt solution may be eluted by passing an L-ascorbic acid 2-phosphate solution through a column containing a zinc type cation exchange resin (preferably a strong cationic exchange resin).

In the case of using anion exchange chromatography, a solution containing L-ascorbic acid 2-phosphate is passed through the anion exchange resin column to adsorb L-ascorbic acid 2-phosphate ion onto the resin, a zinc salt solution is passed therethrough, and the L-ascorbic acid 2-phosphate zinc salt fraction is collected.

In the case where the L-ascorbic acid 2-phosphate solution that is added to the column contains a substance which forms a zinc salt having low solubility, the solution is previously processed to remove such substances (for example, in the case of phosphorus ion, a zinc salt or magnesium salt is added to precipitate and remove the substance). In this manner, the column chromatography can be performed more efficiently.

The chromatography conditions (temperature, flow rate, composition of added solution, concentration, amount of solution, etc.) may be established by taking into account general column chromatography parameters (e.g., column size, physical properties of the resin, exchange capacity, separation capability, viscosity of the added solution, solubility, etc.) well known to those of ordinary skill in the art.

L-ascorbic acid 2-phosphate zinc salt powder can be obtained directly from the above solution containing L-ascorbic acid 2-phosphate zinc salt, or by precipitating or the like in an organic solvent and removing the solvent by spray drying, vacuum drying or freeze drying. When the L-ascorbic acid 2-phosphate zinc salt powder is obtained by precipitating in an organic solvent, the zinc salt added to the column in the anion exchange method preferably, in view of purity, is a salt which is highly soluble in the organic solvent (for example, in the case of using acetone as the organic solvent, zinc chloride or zinc propionate may be used).

The thus-obtained L-ascorbic acid 2-phosphate zinc salt has excellent solubility and is easily formed into an aqueous solution having a concentration of 50 wt % or more. Furthermore, the L-ascorbic acid 2-phosphate zinc salt of the present invention is remarkably stable even under weakly acidic conditions, and a composition containing an L-ascorbic acid 2-phosphate having sufficiently improved stability even in such a pH region can be obtained. Furthermore, a composition also having an antimicrobial effect (including antiseptic, deodorizing and antidandruff effects) can be obtained. Furthermore, vitamin C can be effectively supplied by administering the composition to humans or animals. Examples of the composition include cosmetic preparations, medical preparations, agricultural chemical preparations, animal drug preparations, foodstuff preparations and feedstuff preparations. The ingredients of the composition and the amount of the L-ascorbic acid 2-phosphate zinc salt added thereto are the same as in the case of using a conventional L-ascorbic acid 2-phosphate salt.

For example, a general and preferred range for the content (wt %) of the L-ascorbic acid 2-phosphate zinc salt when added to a cosmetic preparation, a medical preparation, an agricultural chemical preparation, an animal drug preparation, a foodstuff preparation and a feedstuff preparation may be as follows:

| Preparation Type | General | Preferred |
| --- | --- | --- |
| Cosmetic preparation | 0.01–50% | 0.1–5% |
| Medical preparation | 0.01–50% | 0.1–20% |
| Agricultural chemical preparation | 0.01–50% | 0.1–10% |
| Animal drug preparation | 0.01–50% | 0.1–20% |
| Foodstuff preparation | 0.001–50% | 0.002–5% |
| Feedstuff preparation | 0.001–50% | 0.002–5% |

In the case of a salt hydrate, the above amounts are increased to take into account the water of hydration.

EXAMPLES

The present invention is described in greater detail below by reference to the following Examples, however, the present invention should not be construed as being limited thereto.

In the Examples and Test Examples, the analysis of an L-ascorbic acid 2-phosphate salt or an ion thereof was performed using an Ap-containing solution having a known concentration (prepared from L-ascorbic acid 2-phosphate magnesium salt) as a standard by an HPLC method using a Shodex IEC DEAE-825 resin (ammonium acetate 10 mM→1M gradient, detected spectrophotometrically at 265 nm). The elemental analysis was performed by an ICP emission method, flame photometry and an ion chromatography method. Unless otherwise indicated, the reagents used herein were commercially available reagents.

Example 1

Under a nitrogen atmosphere, 10 g of L-ascorbic acid was dissolved in a mixed solvent of 135 ml of water and 15 g of pyridine, and the resulting mixed solution was cooled to 0° C. and adjusted to a pH of 11.5 with a 12% (% by weight, hereinafter the same) potassium hydroxide solution. While keeping the solution at a temperature of from 0 to 5° C., 15 g of phosphorus oxychloride was added by means of a quantitative pump. During the addition, the pH was kept within a range of from 11.45 to 11.55 with a 12% potassium hydroxide solution. After completing the addition, the mixture was stirred at the same temperature for 10 minutes, and 70 ml of a 1.5M magnesium chloride solution was gradually added thereto. The resulting solution was further stirred for 30 minutes, and the precipitate was then removed by suction filtration.

The solution thus obtained was added to a column containing an OH-type anion exchange resin Diaion SA 10A (trade name, manufactured by Mitsubishi Kasei KK) having a column size of 2.5 cm$\phi$×50 cm, and washed with 1 L of water. The running direction of the solution was reversed, 250 ml of a 3M zinc chloride solution was added at a rate of 10 ml/min, and 250 ml of an eluent was obtained. To the eluent, 1 L of acetone was gradually added, and the mixture was stirred for 30 minutes. The precipitate was collected by suction filtration, washed three times with 200 ml of acetone, and vacuum dried to obtain 4.3 g of powder. A small portion of the powder was dissolved in purified water in an amount of 100 ppm and analyzed by the HPLC method described above. As a result, the solution was found to contain Ap in a concentration of 56.7 ppm. Namely, the powder contained Ap in an amount of 56.7%. The elemental analysis for the powder was as follows. C: 16.2%, H: 3.6%, O: 50.2%, P: 7.0%, Zn: 22.3%, Mg: 0.1%, Cl: 0.4%, and K: <0.1%. Thus, the powder was verified to have a purity of 95% or more as $Ap_2Zn_3 \cdot 10H_2O$.

Example 2

To a cation exchange column containing the resin Diaion SK 1B (trade name, manufactured by Mitsubishi Kagaku KK) having a column size of 5 cm$\phi$×25 cm, 1.5 L of 1M sulfuric acid, 0.5 L of water, 1 L of 1M zinc sulfate and 2 L of water were added in sequence at a rate of 20 ml/min to form a zinc type resin.

To the column, 0.5 L of a 10% aqueous solution of L-ascorbic acid PM (L-ascorbic acid 2-phosphate magnesium salt, trade name, produced by Showa Denko KK) and 0.5 L of water were added in sequence at a rate of 10 ml/min, and 1 L of eluent was collected. The eluent thus collected was freeze dried to obtain 52 g of powder. A small portion of this powder was dissolved in purified water in an amount of 100 ppm, and the resulting solution was analyzed by the HPLC method described above. As a result, the solution was found to contain Ap in a concentration of 58.6 ppm. Namely, the powder obtained contained Ap in an amount of 58.6%. The elemental analysis for the powder was as follows. C: 16.7%, H: 3.5%, O: 50.1%, P: 7.2%, Zn: 22.5%, and Mg: <0.1%. Thus, the powder was verified to have a purity of 99% or more as $Ap_2Zn_3 \cdot 9H_2O$.

Unless otherwise indicated, in Test Examples 1 and 2 and in Example 3 below, the L-ascorbic acid 2-phosphate zinc salt obtained in Examples 1 and 2 was used in the following evaluations.

Test Example 1

Stability

The stability of L-ascorbic acid 2-phosphate zinc salt was compared to that of L-ascorbic acid 2-phosphate magnesium salt. Each salt was dissolved in a buffer solution (50 mM acetic acid-NaOH, pH: 5, or 50 mM Tris-HCl, pH: 8). to a concentration of about 0.1% and stored at 50° C. for 476 hours. The concentrations of the L-ascorbic acid 2-phosphate before and after storage were analyzed by the HPLC method.

TABLE 1

| L-ascorbic acid 2-phosphate | Stability (100% = concentration before storage) | |
|---|---|---|
| | pH: 5 | pH: 8 |
| L-ascorbic acid 2-phosphate zinc salt (Example 1) | 91 | 93 |
| L-ascorbic acid 2-phosphate zinc salt (Example 2) | 92 | 95 |
| L-ascorbic acid 2-phosphate magnesium salt | 82 | 95 |

The above results show that the stability of the L-ascorbic acid 2-phosphate zinc salt of the present invention is hardly reduced even when stored under weakly acidic conditions.

Test Example 2

Antimicrobial Effect

To NUTRIENT BROTH (produced by DIFCO), 0.1% of an L-ascorbic acid 2-phosphate salt was added thereto, and the pH was adjusted to 6.8 using hydrochloric acid or sodium hydroxide. Using 5 ml of the medium thus prepared, test bacterium were inoculated in a concentration of about $10^7$ cells/ml and incubated in a test tube at 37° C. for 24 hours. The results are shown in Table 2 below. In Table 2, "+" indicates that turbidity increased after incubation, and "−" indicates no increase in turbidity. As a control, the same test was performed using a medium not containing an L-ascorbic acid 2-phosphate salt.

TABLE 2

| | Test bacterium | |
|---|---|---|
| L-Ascorbic acid 2-phosphate | E. coli (K-12 strain) | B. subtilis (168 strain) |
| Zinc salt (Example 1) | − | − |
| Zinc salt (Example 2) | − | − |
| Magnesium salt | + | + |
| Sodium salt | + | + |
| Not added | + | + |

The above results show that the L-ascorbic acid 2-phosphate zinc salt of the present invention has antimicrobial properties.

Example 3

Cosmetic Preparation

One example of a cosmetic preparation in accordance with the present invention is shown below.

TABLE 3

| Ingredient | % by weight |
|---|---|
| (A) Liquid paraffin | 5.0 |
| Hexalan (produced by Kyoei Kagaku Kogyo | 3.0 |

TABLE 3-continued

| Ingredient | % by weight |
|---|---|
| KK) | |
| Paraffin | 4.0 |
| Beeswax HP (produced by Kyoei Kagaku Kogyo KK) | 4.0 |
| Sorbitan monostearate | 1.0 |
| Polyoxyethylene (5) sorbitan monostearate | 3.0 |
| Glycerin monostearate | 1.0 |
| (B) Glycerin | 4.0 |
| L-ascorbic acid 2-phosphate zinc salt (Example 1) | 3.0 |
| β-Cyclodextrin | 1.0 |
| Water | 70.8 |
| (C) Perfume | 0.2 |

Ingredient (A) and Ingredient (B) each was heated at 80° C., then mixed and stirred. After cooling to 50° C., Ingredient (C) was added, and the ingredients were mixed by further stirring to prepare a homogeneous cream.

Example 4
Medical Preparations

| (1) Preparation for an injectable drug (e.g., a drug for supplementing vitamin C) | |
|---|---|
| L-ascorbic acid 2-phosphate zinc salt (Example 1) | 1.0 wt % |
| glucose | 5 wt % |
| distilled water | 94 wt % |

The above ingredients were dissolved in distilled water and sterilized by filtering through a membrane filter with a pore size of 0.2 μm.

| (2) Preparation for an oral capsule drug (e.g., an antiulcer drug) | |
|---|---|
| L-ascorbic acid 2-phosphate zinc salt (Example 1) | 10 wt % |
| corn starch | 85 wt % |
| magnesium stearate | 5 wt % |

The above ingredients were thoroughly mixed using a mill, and 100 mg of the mixture was inserted into a gelatin capsule.

| (3) Preparation for an oral powder drug (e.g., an antiulcer drug) | |
|---|---|
| L-ascorbic acid 2-phosphate zinc salt (Example 1) | 10 wt % |
| crystalline lactose | 90 wt % |

The above ingredients were thoroughly mixed using a mill.

| (4) Preparation for an ointment drug (e.g., a drug for acne treatment) | |
|---|---|
| L-ascorbic acid 2-phosphate zinc salt (Example 1) | 5 wt % |
| squalene | 10 wt % |
| stearic acid | 10 wt % |
| propyleneglycol monostearate | 3 wt % |
| polyoxyethylene cetyl ether | 1 wt % |
| propyleneglycol | 15 wt % |
| methyl p-hydroxybenzoate | 0.2 wt % |
| distilled water | 55.8 wt % |

The above ingredients were mixed and stirred at 80° C. to obtain a homogeneous ointment.

Example 5
Feedstuff Preparations

| (1) Preparation for a feed additive for cattle, chicken, dogs and cats (e.g., a vitamin C supplement) | |
|---|---|
| L-ascorbic acid 2-phosphate zinc salt (Example 1) | 0.06 wt % |
| wheat bran | 30 wt % |
| barley meal | 20 wt % |
| rice bran | 42 wt % |
| soybean meal | 5 wt % |
| sodium chloride | 0.5 wt % |
| vitamin mixture (not containing vitamin C) | 2.44 wt % |

The above ingredients were mixed and pelleted using a pelletter at 80° C. and dried at 100° C.

| (2) Preparation for a feed additive for fish (e.g., a vitamin C supplement) | |
|---|---|
| L-ascorbic acid 2-phosphate zinc salt (Example 1) | 0.01 wt % |
| fish meal | 56 wt % |
| salmon milt | 6 wt % |
| squid liver oil | 5 wt % |
| soybean lecithin | 4 wt % |
| valine | 0.3 wt % |
| isoleucine | 0.2 wt % |
| corn starch | 5 wt % |
| mineral mixture | 5 wt % |
| gluten | 8 wt % |
| vitamin mixture (not containing vitamin C) | 2.59 wt % |
| ω3-HUEA | 1 wt % |
| soybean meal | 6.9 wt % |

The above ingredients were mixed and pelleted using a pelletter at 80° C. and dried at 100° C.

Example 6
Foodstuff Preparation

| (1) Preparation for a food additive (e.g., a vitamin C supplement) | |
|---|---|
| L-ascorbic acid 2-phosphate zinc salt (Example 1) | 10 wt % |
| citric acid disodium salt | 0.5 wt % |
| oligosugar | 89.5 wt % |

The above ingredients were thoroughly mixed using a mill.

The L-ascorbic acid 2-phosphate zinc salt of the present invention is highly soluble and stable under weakly acidic conditions, and also has antimicrobial properties. By adding the salt to cosmetic preparations, medical preparations, agricultural chemical preparations, animal drug preparations, foodstuff preparations and feedstuff preparations, a vitamin C-containing preparation having improved solubility and stability and having an antimicrobial effect can be obtained.

While the invention has been described in detail and with reference to specific embodiments thereof, it will be apparent to one skilled in the art that various changes and modifications can be made therein without departing from the spirit and scope thereof.

What is claimed is:

1. An anti-microbial composition comprising L-ascorbic acid 2-phosphate zinc salt of formula (1):

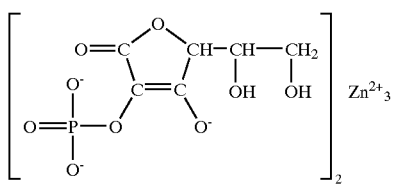

(1)

or a hydrate of formula (2):

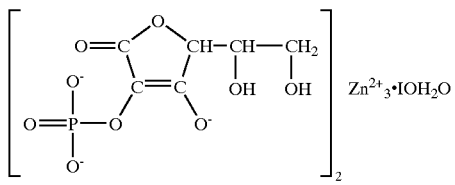

(2)

as an active ingredient and a pharmaceutically acceptable carrier or diluent, and wherein the L-ascorbic acid 2-phosphate zinc salt is in an amount of 0.01–50 weight percent when the composition is a cosmetic preparation, a medical preparation, an agricultural chemical preparation or an animal drug preparation, or in an amount of 0.001–50 percent weight when the composition is a foodstuff preparation or a feedstuff preparation, and further wherein when the L-ascorbic acid 2-phosphate zinc salt is a hydrate, the final weight percent concentration of the composition is adjusted for the water of the hydrate.

2. The anti-microbial composition as claimed in claim 1, wherein 95 mol % or more of the entire cationic charge of said salt or hydrate thereof constitutes zinc ion and 95 mol % or more of the entire anionic charge of said salt or hydrate thereof constitutes L-ascorbic acid 2-phosphate ion.

3. The anti-microbial composition as claimed in claim 1, wherein said composition is selected from the group consisting of a cosmetic preparation, a medical preparation, an agricultural chemical preparation, an animal drug preparation, a foodstuff preparation and a feedstuff preparation.

4. The anti-microbial composition as claimed in claim 1, wherein said composition is an injectable solution comprising L-ascorbic acid 2-phosphate zinc salt or a hydrate thereof, and said pharmaceutically acceptable carrier or dilutent is glucose and water.

5. The anti-microbial composition as claimed in claim 1, containing L-ascorbic acid 2-phosphate zinc salt in an amount of 0.1–5 wt % when the composition is a cosmetic preparation, in an amount of 0.1–20 wt % when the composition is a medical preparation, in an amount of 0.1–10 wt %, when the composition is an agricultural chemical preparation, in an amount of 0.1–20 wt % when the composition is an animal drug preparation, in an amount of 0.002–5 wt % when the composition is a foodstuff preparation or a feedstuff preparation, and in the case of a hydrate salt of L-ascorbic acid 2-phosphate zinc salt, the above amounts are adjusted to take into account the water of the hydrate.

6. The anti-microbial composition as claimed in claim 1, containing L-ascorbic acid 2-phosphate zinc salt in an amount of 0.1–5 wt % when the composition is a cosmetic preparation, and in the case of a hydrate salt of L-ascorbic acid 2-phosphate zinc salt, the above amount is adjusted to take into account the water of the hydrate.

7. The anti-microbial composition as claimed in claim 1, containing L-ascorbic acid 2-phosphate zinc salt in an amount of 0.1–20 wt % when the composition is a medical preparation, and in the case of a hydrate salt of L-ascorbic acid 2-phosphate zinc salt, the above amount is adjusted to take into account the water of the hydrate.

8. An anti-microbial composition comprising L-ascorbic acid 2-phosphate zinc salt of formula (1):

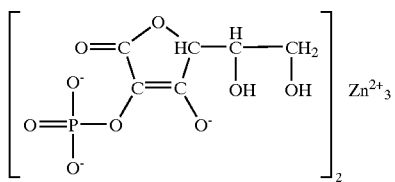

(1)

or a hydrate of formula (2):

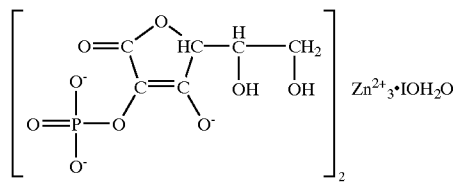

(2)

as an active ingredient and a pharmaceutically acceptable carrier or diluent, wherein said composition is a member selected from the group consisting of a medical preparation, an agricultural chemical preparation, an animal drug preparation, a foodstuff preparation, and a feedstuff preparation; and wherein the L-ascorbic acid 2-phosphate zinc salt is in an amount of 0.01–50 weight percent when the composition is a medical preparation, an agricultural chemical preparation, or an animal drug preparation, or in an amount of 0.001–50 percent weight when the composition is a foodstuff preparation or a feedstuff preparation, and further wherein when the L-ascorbic acid 2-phosphate zinc salt is a hydrate, the final weight percent concentration of the composition is adjusted for the water of the hydrate.

9. The anti-microbial composition as claimed in claim 8, wherein 95 mol % or more of the entire cationic charge of said salt or hydrate thereof constitutes zinc ion and 95 mol % or more of the entire anionic charge of said salt or hydrate thereof constitutes L-ascorbic acid 2-phosphate ion.

10. The anti-microbial composition as claimed in claim 8, wherein said composition is an injectable solution comprising L-ascorbic acid 2-phosphate zinc salt or a hydrate thereof, and said pharmaceutically acceptable carrier or diluent is glucose and water.

11. The anti-microbial composition as claimed in claim 8, containing L-ascorbic acid 2-phosphate zinc salt in an amount of 0.1–20 wt % when the composition is a medical preparation, in an amount of 0.1–10 wt % when the composition is an agricultural chemical preparation, in an amount of 0.1–20 wt % when the composition is an animal drug preparation, in an amount of 0.002–5 wt % when the composition is a foodstuff preparation or a feedstuff preparation, and in the case of a hydrate salt of L-ascorbic acid 2-phosphate zinc salt, the above amounts are adjusted to take into account the water of the hydrate.

12. The anti-microbial composition as claimed in claim 8, containing L-ascorbic acid 2-phosphate zinc salt in the amount of 0.1–20 wt % when the composition is a medical preparation, and in the case of a hydrate salt of L-ascorbic acid 2-phosphate zinc salt, the above amount is adjusted to take into account the water of the hydrate.

13. An anti-microbial composition comprising L-ascorbic acid 2-phosphate zinc salt of formula (1):

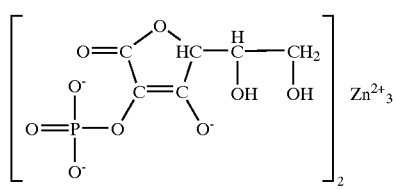

(1)

or a hydrate of formula (2):

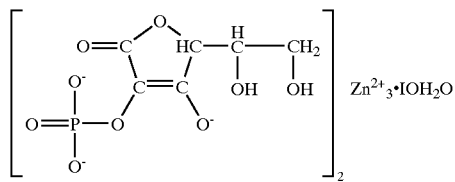

(2)

as an active ingredient and a pharmaceutically acceptable carrier or diluent, wherein the composition is stable in a pH of from 5 to 8, and wherein the L-ascorbic acid 2-phosphate zinc salt is in an amount of 0.01–50 weight percent when the composition is a cosmetic preparation, a medical preparation, an agricultural chemical preparation, or an animal drug preparation, or in an amount of 0.001–50 percent weight when the composition is a foodstuff preparation or a feedstuff preparation, and further wherein when the L-ascorbic acid 2-phosphate zinc salt is a hydrate, the final weight percent concentration of the composition is adjusted for the water of the hydrate.

14. The anti-microbial composition as claimed in claim 13, wherein 95 mol % or more of the entire cationic charge of said salt or hydrate thereof constitutes zinc ion and 95 mol % or more of the entire anionic charge of said salt or hydrate thereof constitutes L-ascorbic acid 2-phosphate ion.

15. The anti-microbial composition as claimed in claim 13, wherein said composition is selected from the group consisting of a cosmetic preparation, a medical preparation, an agricultural chemical preparation, an animal drug preparation, a foodstuff preparation, and a feedstuff preparation.

16. The anti-microbial composition as claimed in claim 13, wherein said composition is an injectable solution comprising L-ascorbic acid 2-phosphate zinc salt or a hydrate thereof, and said pharmaceutically acceptable carrier or diluent is glucose and water.

17. The anti-microbial composition as claimed in claim 13, containing L-ascorbic acid 2-phosphate zinc salt in the amount of 0.1–5 wt % when the composition is a cosmetic preparation, in an amount of 0.1–20 wt % when the composition is a medical preparation, in an amount of 0.1–10 wt % when the composition is an agricultural chemical preparation, in an amount of 0.1–20 wt % when the composition is an animal drug preparation, in an amount of 0.002–5 wt % when the composition is a foodstuff preparation or a feedstuff preparation, and in the case of a hydrate salt of L-ascorbic acid 2-phosphate zinc salt, the above amounts are adjusted to take into account the water of the hydrate.

18. The anti-microbial composition as claimed in claim 13, containing L-ascorbic acid 2-phosphate zinc salt in the amount of 0.1–20 wt % when the composition is a medical preparation and in the case of a hydrate salt of L-ascorbic acid 2-phosphate zinc salt, the above amounts are adjusted to take into account the water of the hydrate.

* * * * *